United States Patent [19]

Newman et al.

[11] Patent Number: 5,258,386

[45] Date of Patent: Nov. 2, 1993

[54] (+)-3-SUBSTITUTED-N ALKYLMORPHINANS, SYNTHESIS AND USE AS ANTICONVULSANT AND NEUROPROTECTIVE AGENTS

[75] Inventors: Amy H. Newman, Silver Spring; Frank C. Tortella, Columbia, both of Md.

[73] Assignee: The United States of America as represented by the Secretary of the Army, Washington, D.C.

[21] Appl. No.: 715,084

[22] Filed: Jun. 5, 1991

[51] Int. Cl.$^5$ ............................................. A61K 31/485
[52] U.S. Cl. ...................................... 514/289; 546/74; 544/287
[58] Field of Search .......................... 546/74; 514/289

[56] References Cited

FOREIGN PATENT DOCUMENTS 0540913  5/1957  Canada .................................. 546/74

OTHER PUBLICATIONS

Gates, et al., J. Am. Chem. Soc., vol. 80, pp. 1186–1194 (1958).
Conrow, et al., Steroids, vol. 11, No. 2, pp. 151–164 (1968).
Hori, et al. Chemical Abstracts, vol. 85, 63215z (1976).

*Primary Examiner*—Donald G. Daus
*Attorney, Agent, or Firm*—Werten F. W. Bellamy; John F. Moran

[57] ABSTRACT

It has been discovered that certain (+)-3-substituted-N-alkylmorphinans are effective anticonvulsant and neuroprotective agents. Novel compounds having these biological properties are presented in a method of use for preventing, treating or controlling convulsions in mammals having a need for such treatment. The compounds do not lead to dependency, have low toxicity, and provide effective anticonvulsant or neuroprotective treatment with little or no behavioral detriment to the recipient. A number of pharmacological formulations and methods of administering compounds of the invention are suitable for anticonvulsive or neuroprotective treatments.

10 Claims, 2 Drawing Sheets

(+)-3-SUBSTITUTED-N ALKYLMORPHINANS, SYNTHESIS AND USE AS ANTICONVULSANT AND NEUROPROTECTIVE AGENTS

BACKGROUND OF THE INVENTION

1. Technical Field

This invention pertains to a group of novel compounds which exhibit anticonvulsant and neuroprotective properties, methods for their use in controlling seizures or convulsions, and methods of preparing these compounds. The novel compounds of the invention are (+)-3-substituted-N-alkylmorphinans which have been found to have anticonvulsant and neuroprotective properties, their acid addition salts, and pharmaceutical applications for the prevention, treatment and control of seizures and convulsions.

2. Description of Related Art

Morphinans are the parent substance of morphine alkaloids such as codeine and thebaine. Morphine alkaloids and their derivatives have many uses as narcotic analgesics. The basic morphinan structure is similar to the basic morphine structure, but comprehends two configurational isomeric forms, shown in formulas I and II below:

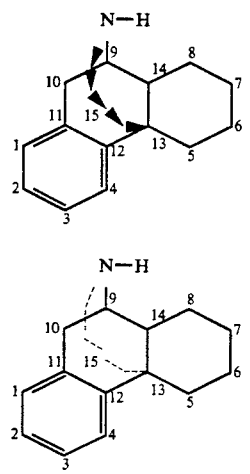

In these formulas, broken lines represent covalent bonds which project below the plane of the reference atoms, while solid wedges or heavily accented lines signify covalent bonds which project above the plane. With this in mind, Formula I, is the L (levorotatory) or (−) enantiomeric form of the basic morphinan structure. Derivatives of this form occur in nature. The enantiomeric morphinan basic structure shown in formula II is the D (dextrorotatory) or (+) isomer, and its derivatives are rarely available in nature, even in trace quantities, and thus can be obtained only, if at all, by means of synthetic preparations.

Derivatives of the antipedal morphinan structures differ markedly in pharmaceutical utility and in the respective mechanisms of their biological activities. The analgesic properties of morphine and of its related naturally occurring (−)-morphinan compounds for treating moderate to severe pain are known. It is presently understood that the biological activity of these compounds results from their binding to the opiate receptor in the central nervous system. Some examples of pharmaceutical uses of compounds belonging to the (−)-morphinan series, the natural opioids, include analgesics (U.S. Pat. No. 3,981,874), and combined analgesic and narcotic antagonist for treating drug dependency (U.S. Pat. Nos. 4,272,540; 4,362,733; and 4,489,079). While the natural opioids have profoundly effective analgesic properties and remain in widespread use, there are serious liabilities associated with their use since natural opioids are narcotic. Use of the natural opioids may induce dependency and other detrimental side effects. Furthermore, tolerance may lead to requirements for increasingly large dosages just to maintain desired analgesic levels.

On the other hand, it has been reported that the unnatural (+)-morphinans bind to distinct receptors in the central nervous system which are different from opiate binding sites. Dextromethorphan, (+)-3-methoxy-N-methylmorphinan, for example, has been found to be a potent antitussive agent (U.S. Pat. No. 4,552,962). More recently, it has been reported by Jose Musacchio and Frank Tortella in U.S. Pat. No. 4,898,860 and Michael Pontecorvo and John Ferkany in U.S. Pat. No. 4,906,638 that dextromethorphan has a potentiating effect on certain antiepileptic or antiseizure compounds such as diphenylhydantoin, phenobarbital, diazepam ketamine, and carbamazepine. The pharmacological use of dextromethorphan has at least one major disadvantage, however, in that it metabolizes rapidly by demethylation in vivo, to dextrorphan, (+)-3-hydroxy-N-methylmorphinan. Dextrorphan is the major dextromethorphan metabolite in man, and has been documented to cause harmful behavioral side effects in addition to having some anticonvulsant activity. Dextromethorphan is not very potent as an anticonvulsant agent and the higher dosages that might be required for desired convulsion control would in turn cause in vivo biosynthesis of dextrorphan by dextromethorphan metabolism, with the attendant detrimental symptoms. At elevated doses, dextromethorphan actually becomes proconvulsant.

Other anticonvulsant agents and combinations are known, but toxicity and other dosage-dependent symptoms remain as challenges to the pharmacological control of epileptic seizures and other kinds of convulsions. Another manifestation of this symptomatology is the interference by some anticonvulsants with the availability in vivo of hydroxycholecalciferol and dihydroxycholecalciferol, metabolic prohormonal forms of vitamin D, evidently caused by the degradation of vitamin D and its metabolites prior to absorption. Other side effects of anticonvulsant treatments include hepatotoxicity and teratogenicity. Furthermore, dextromethorphan and other known anticonvulsion or antiseizure agents are typically effective against only a narrow range of seizure types, leaving some seizure types void of effective control treatment altogether.

It is impossible to predict on the basis of molecular structure alone whether a particular morphinan will have any pharmacological utility. It is apparent that even minute modifications in the composition of the molecule can result in significant changes in pharmacological activity between two structurally similar species. Thus a morphinan belonging to the unnatural series of opioids which possesses the appropriate profile of anticonvulsant and/or neuroprotective actions has potential for treatment or control of convulsions or seizures, or neuroprotection, without the liabilities of drug dependence, drug abuse, or toxic symptoms.

Accordingly, there is a need in the field for the development of anticonvulsant agents that have minimal toxicity and produce few, if any, harmful side effects while being effective against a wide range of seizure types. More specifically, there is a need for anticonvulsant and neuroprotective agents that are effective at dosages that minimize or eliminate drug dependency, poisoning, and other harmful or undesirable side effects.

The present invention provides novel compounds with surprising anticonvulsant, antiseizure and neuroprotective properties, processes for synthesizing novel compounds, and pharmacological methods for using them, without dependence, behavioral modification, toxicity, undesirable side effects, or other liabilities that characterize prior art compounds and treatment methods.

SUMMARY OF THE INVENTION

It has been discovered that certain (+)-3-substituted-N-alkylmorphinans derived from the basic (+)-morphinan structure are biologically active in the treatment of convulsions, seizures and other neurological disorders that result in convulsions or seizures. These compounds, their pharmaceutical salts, and formulations containing them may be used to treat convulsions and seizures in recipients requiring such treatment while reducing adverse side effects such as iatrogenic dependency, toxic symptoms, and behavioral detriments.

This invention is directed primarily to a group of compounds which have anticonvulsant and/or neuroprotective activity. The invention further relates to a method of treating epilepsy, convulsions, seizures, or ischemia using the compounds. In yet another aspect, the invention is directed to methods for preparing novel compounds of the invention.

Accordingly, the present invention relates to novel compounds and their pharmaceutical salts and formulations, as well as a method of treatment comprising the pharmacological administration of the compounds of the invention which is an effective method of seizure and convulsion control as well as neuroprotection in recipients requiring such treatment. The invention is also directed to processes for preparing novel compounds of the invention.

DETAILED DESCRIPTION OF THE INVENTION

Figure 1:
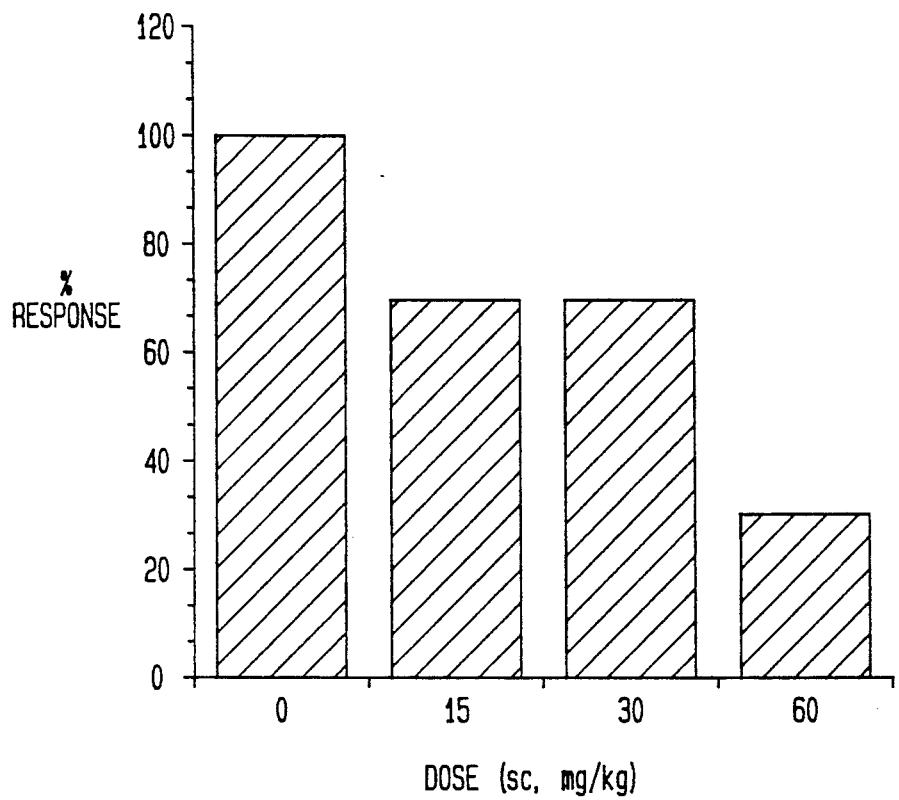
FIG. 1 is a bar diagram showing the presence of seizure activity as a function of the amount of dextromethorphan administered.

The present inventors have prepared a group of novel compounds and have discovered that the novel compounds have potent anticonvulsant and neuroprotective properties. In addition to treating, preventing or controlling convulsions, the compounds of the invention have neuroprotective activity with respect to nervous system disorders that have biochemical mechanisms which share common traits with those of seizure or convulsive disorders. For example, some ischemic disorders caused by concussive injuries to the head result in seizures which may be treated by compounds which are N-methyl-D-aspartate (NMDA) neuroreceptor site antagonists (both competitive and non-competitive) (*Medicinal Res. Rev.* 9:1-23, 1989; *Trends in Neuroscience* 10(7), Elsevier 1987). In such instances, an anticonvulsant compound of the invention would also be found to possess antiischemic activity. The compounds of the invention have useful pharmacological activity without inducing dependency, while reducing or eliminating harmful side effects. Because of the potency of the compounds, lower doses are effective for anticonvulsant compounds of the invention than are required for prior art anticonvulsant compounds. A method for treating convulsions using compounds of the invention has been developed in accordance with these discoveries. In addition, processes for preparing the novel compounds of the invention have been discovered and tested to prove their utility in synthesizing the compounds described in more detail below.

The compounds of this invention are (+)-3-substituted-N-alkylmorphinans (-17-alkylmorphinan may be used interchangeably in the nomenclature) which have anticonvulsant and/or neuroprotective properties as established by testing with laboratory animals. Preferred compounds of the invention are more potent than prior art compounds and provide therapeutic treatment without the undesired side effects that characterize compounds of the prior art. The invention is also directed to methods of using the novel compounds in a variety of pharmaceutical formulations.

The compounds of the present invention have the following formula:

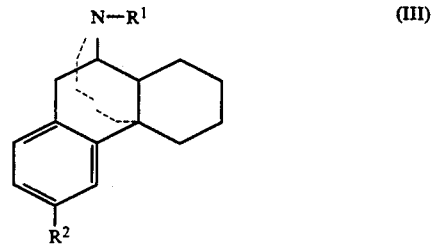

(III)

in which $R^1$ is methyl, ethyl, methylcyclopropyl, allyl, adamantyl (i.e., tricyclo[3.3.1.1.$^{3,7}$]decyl), or $CH_2CH_2OCH_2CH_2N(CH_2CH_3)_2$, and $R^2$ is hydrogen, amino, isothiocyanato, chloro, bromo, fluoro, methylamino, dimethylamino, NHC(=NH)NH$_2$, NHC(=NH)NH-phenyl, or NHC(=NH)NH-adamantyl. The ring numbering system is the same as that demonstrated above in formulas I and II.

An anticonvulsant or neuroprotective morphinan derivative of this invention may be administered alone or as part of a pharmaceutical formulation, and in either case administration may be by any suitable route including oral, rectal, nasal, topical (including buccal and sublingual), and parenteral (including subcutaneous, intramuscular, intravenous and intradermal) with oral or parenteral being preferred. It will be appreciated that the preferred route may vary with, for example, the condition and age of the recipient. A preferred dose is 1000 mg or less of a compound of the invention as active ingredient alone or in a pharmaceutical formulation.

It is preferable to present the active anticonvulsant and neuroprotective morphinan derivatives of this invention as part of a pharmaceutical formulation. The formulations of this invention comprise at least one administered ingredient, as defined above, together with one or more acceptable carriers, flavorings or coatings where suitable, and optionally other therapeutic agents. The carrier(s) must be acceptable in the sense that they must be compatible with the other ingredients of the formulation and they must not be harmful to the recipient.

The formulations may conveniently be presented in unit dosage form and may be prepared by any methods practiced in the art of pharmacy. In general, formulations are prepared by bringing the active ingredients into association with finely divided solid carriers, liquid carriers, or both, and then, if necessary or desired, shaping the product. Formulations useful in the practice of the present invention which are suitable for oral administration may be presented as discrete units such as capsules, cachets, or tablets containing a predetermined amount of the active ingredient; as a powder or granules; as a solution or suspension in an aqueous or non-aqueous liquid. Preferred unit-dosage forms are liquid formulations for injection or oral administration, and tablets, lozenges, capsules or cachets, also suitable for oral administration.

Compressed tablets may be prepared by compressing with suitable means the active ingredients in a free-flowing form such as a powder or granules, optionally mixed with a binder, lubricant, diluent, preservative, surface-active or dispersing agent. Molded tablets may be prepared with suitable molding means such as punching or compressing the active ingredient and any binders or fillers in a tabletting machine. A mixture of the powdered compound moistened with an inert liquid diluent may also be used. Tablets may be optionally coated or scored and may be formulated so as to provide slow or controlled release of the active ingredient contained in the tablet. Tablets may optionally contain other ingredients, such as additional therapeutic agents. Soft shell gelatin capsules used as pharmaceutical coatings are suitable for orally administered formulations of this invention, also.

A suitable formulation for nasal administration may include a carrier comprising a solid, coarse powder having particulate size averaging 20 to 500 microns in diameter. Such a formulation would be administered by rapid inhalation through the nasal passage, for example, from a container of the powder held close to the nose. Suitable formulations including a liquid carrier might include aqueous or oily solutions of the active ingredient. A preferred system of delivery for nasal administration is a nasal spray.

Suitable formulations for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents and thickening agents. The formulations may be presented in unit-dose or multi-dose containers, for example sealed ampoules and vials including those suitable for disposal after use, and may be stored in a freeze-dried (lyophilized) condition requiring only the addition of the sterile liquid carrier, such as water for injections, immediately prior to use. Extemporaneous injection solutions and suspensions may be prepared from sterile powders, granules and tablets of the kind previously described.

Preferred unit-dose formulations are those that contain a daily dose or unit, daily sub-dose or appropriate fractional dose or sub-dose, of the administered ingredient. Formulations comprising the compounds of this invention may include other agents conventional in the art pertaining to the type of formulation in question. For example, formulations suitable for oral administration may include flavoring agents or coatings to facilitate swallowing or to mask an unpleasant taste if a flavoring is not used or is not completely effective. This invention covers the compounds listed above which belong to the unnatural (dextrorotatory) or (+) series of alkylmorphinans, showing useful anticonvulsant or neuroprotective activity in the form of their free bases or appropriate salts, such as hydrochlorides, oxalates, tartrates, fumarates, etc., by standard pharmacological testing.

Effective methods of synthesizing compounds of the invention will be described in relation to the reaction schemes and the synthetic examples set forth below.

SYNTHESIS

Chemistry

Melting points were determined on a Thomas-Hoover capillary melting point apparatus and are uncorrected. $^1$H NMR spectra were obtained either on a Bruker AC 300 MHz or a Varian XL 300 MHz spectrometer with trimethylsilane as the internal standard. $^{13}$C NMR spectra were obtained on a Bruker AC 300 MHz spectrometer. IR spectra were determined on a Nicolet 105 IR spectrometer using either KBr pellets or $CHCl_3$ cells. EIMS and CIMS ($NH_3$ ionization) were obtained on a Finnegan 1015 mass spectrometer. For purification, flash column chromatography (silica gel, grade 60, 230–400 mesh, Aldrich Chemical Company, Milwaukee, Wis.) was used. Product homogeneity was detected by thin layer chromatography (silica gel GF, Analtech, Del.); the solvent system for chromatography was $CHCl_3:CH_3OH:NH_4OH$ (90:10:1) unless otherwise noted. All compounds gave NMR, IR and MS data consistent with the structures assigned. Elemental analyses were performed by Spang Micro Analytical Laboratory, Eagle Harbor, Mich., and were within 0.4% of theoretical values.

For brevity in the following discussion, chemical compounds which appear herein will be identified by reference numerals which will apply consistently to their respective corresponding species throughout the reaction scheme diagrams, examples, etc. that follow. The numerals correspond to compounds as indicated in the following table, using formula III as the basic reference structure.

TABLE 1

| Reference Numeral | $R^1$ | $R^2$ |
|---|---|---|
| 1 | —CH$_3$ | —OCH$_3$ |
| 2 | —CH$_3$ | —OH |
| 3 | —CH$_3$ | -2-phenyl-4-quinazolinyloxy |
| 4 | —CH$_3$ | -4-oxo-2-phenyl-3(4H)-quinazolinyl |
| 5 | —CH$_3$ | —NH$_2$ |
| 6 | —CH$_3$ | —CHCH$_3$ |
| 7 | —CH$_3$ | —N(CH$_3$)$_2$ |
| 8 | —CH$_3$ | —Cl |
| 9 | —CH$_3$ | —NCS |

In the syntheses of compounds of the invention described in the following examples and reaction schemes, dextrorphan, 2, was prepared from dextromethorphan, 1, and used as the starting material. Some known synthetic techniques, documented herein, were applied at stages of the multistep syntheses, having been modified as needed, to develop novel processes for synthesizing the novel compounds of the invention. The O-demethylation of 1 with 48% HBr yielded 2. Treatment of 2 with 4-chloro-2-phenylquinazoline (which is sold under the trademark "AM-ex-OL" belonging to Aldrich Chemical Company) resulted in excellent yields of the ether intermediate, 3. The ether 3 could be used directly in the next stage of synthesis or could be recrystallized in ethyl acetate. Heating 3 neat in accordance with the technique described in Steroids 11: 151 [1968] resulted in decomposition of the ether. The ether was converted to 4 in moderate yield by using mineral oil as the solvent. Basic hydrolysis to an iminocarboxylic acid intermediate followed by acidic hydrolysis yielded 5 which was purified with HCl salt. Scheme I shows how (+)-3-amino-N-methylmorphinan (compound 5) is prepared. This product was monomethylated with 37% formaldehyde and succinimide followed by sodium borohydride reduction (*J.Org.Chem.* 38:1348, 1973) to give 6, purified as dioxalate salt, in moderate yield. Dimethylation of 6 with 37% formaldehyde and sodium cyanoborohydride reduction (*J.Org.Chem.* 37:1673, 1972) gave a good yield of 7, isolated as the sesquitartrate salt. Compound 5, the 3-amino derivative of formula III, was converted to 8 by treating 5 with t-butylnitrite and cuprous chloride as in *J.Org.Chem.* 42:2426, 1977. Purification by flash column chromatography was followed by formation of the fumarate salt. Treatment of 5 with thiophosgene using standard methods (*Nature* 278:854, 1979) gave 9 in moderate yield, purified as the HCl salt. Scheme II shows how these compounds are prepared from compound 5. Other compounds of the invention for which synthesis is not specifically described in a working example may be prepared by following the techniques described in the literature cited herein-above and in the examples set forth below. All cited literature is incorporated by reference.

The following examples further illustrate this invention.

EXAMPLE 1

(+)-3-(2-Phenyl-4-quinazolinyloxy)-17-methylmorphinan

The O-demethylation procedure described in *Steroids* 11:151 [1968] was modified for this synthesis. First, 16.1 g (62.3 mmol) of dextrorphan, 2, were dissolved in 500 mL hot acetone, to which 15.5 g (64.4 mmol) AM-ex-OL (Aldrich) and 17.13 g (123.9 mmol) potassium carbonate were added. The reaction mixture was stirred at reflux overnight under an atmosphere of argon. After cooling, the reaction mixture was poured into a separatory funnel to which 500 mL water were added. Extraction with 1×500 and 2×250 mL benzene was followed by washing the combined organics with 1×250 mL water and removing the solvent in vacuo to give 27.51 g (96%) product as a white glass which was homogeneous by TLC. Recrystallization in ethyl acetate gave pure 3 as white crystals, mp 138°-139° C. EIMS m/z 461. Anal. ($C_{31}H_{31}N_3$) C, H, N.

EXAMPLE 2

(+)-3-[4-Oxo-2-phenyl-3(4H)-quinazolinyl]-17-methylmorphinan

Compound 3 (10.0 g, 21.7 mmol) was placed in 100 mL mineral oil (light white oil, Sigma), under a stream of argon and was stirred vigorously and carefully heated in a sand bath to 330°-340° C. Complete conversion to 4 occurred in 8–10 hours. The reaction proceeds significantly slower at reduced temperatures and the mixture decomposes at temperatures above 350° C. The yellow reaction mixture was allowed to cool to room temperature and was suction filtered through a pad of "flash" silica gel. The mixture was eluted with 700 mL ether to remove all mineral oil and the receiving flask was changed and the product was eluted with 800 mL $CHCl_3:CH_3OH:NH_4OH$ (90:10:1) to give 5.95 g (60%) yellow foamy product that was homogeneous by TLC. This intermediate was not crystalline and therefore was characterized spectrally and taken to the next step without further purification. IR 1690 (C=O) $cm^{-1}$; EIMS 461 m/z.

EXAMPLE 3

(+)-3-Amino-17-methylmorphinan di-HCl

To a solution of 4.89 g (10.7 mmol) of 4 in 100 mL absolute ehtanol, 30 mL 4N sodium hydroxide were added and the reaction mixture was allowed to stir at reflux, under an atmosphere of argon. After 18 hours, TLC showed complete loss of 4. The reaction mixture was cooled in an ice bath, and carefully acidified to pH 2 with conc. hydrochloric acid. An additional 100 mL of 1N hydrochloric acid were added and the reaction mixture was stirred at reflux under an atmosphere of argon for 1.5 hours. After cooling in an ice bath the aqueous reaction mixture was extracted with 1×200 and 2×100 mL ether. The ether fraction was washed with 1×200 mL 1N hydrochloric acid and the combined aqueous fraction was neutralized to pH 9 with ammonium hydroxide. Extraction with 1×200 mL and 1×100 mL chloroform followed by 1×100 mL chloroform/methanol (4:1) and removal of solvent in vacuo resulted in 2.53 g (93%) crude 5 as a white foamy free base. The free base was dissolved in a minimal volume of hot methanol and acidified with a saturated solution of hydrochloric acid in 2-propanol, addition of ether resulted in an oily product, but removal of solvent followed by recrystallization in methanol/ether resulted in 1.0 g (34%) 5 as white crystals, d 280° C. The mother liquor was neutralized and purified by flash column chromatography (CMA 95:5:1) to give 0.84 g (31%) pure base as a white foam. IR (free base, chloroform) 3400 (d, $NH_2$); $^1H$ NMR ($CDCl_3$) d 6.90 (d, J=4 Hz, 1H), 6.60 (d, j=1 Hz, 1H), 6.50 (dd, J=4, 1 Hz, 1H), 3.55 (brs, 2H), 2.60 (S, 3H); CIMS M+H 257 m/z. Anal. ($C_{17}H_{24}N_2HCl$) C, H, N.

EXAMPLE 4

(+)-3-Methylamino-17-methylmorphinan dioxalate

To a solution of 0.76 g (3 mmol, free base) 5 in 8 mL absolute ethanol, 0.3 mL 37% formaldehyde and 0.45 g (4.5 mmol) succinimide was added. The reaction mixture was stirred at reflux under an atmosphere of argon for 2 hours. The volatiles were evaporated, the residue was redissolved in 3 mL DMSO and 0.18 g (4.7 mmol) sodium borohydride was added at room temperature. The reaction mixture was warmed to 100° C., stirred for 15 minutes, and then allowed to cool. Extraction with 25 mL water and 3×25 mL methylene chloride was followed by washing the combined organics with 3×20 mL water, drying with sodium sulfate, and evaporating to 0.50 g (63%) of white foam that was nearly homogeneous by TLC (CMA 90:10:1). The foamy free base was dissolved in a minimal volume of hot methanol and 0.33 g (3.7 mmol, 2 eq) oxalic acid was added (pH 4). The crystalline product was isolated and recrystallized in methanol to give 0.51 g 6, mp 187°-193° C. IR (salt, KBr) 2400 (broad NH+); $^1$H NMR (CDCl$_3$) d 6.92 (d, J=4 Hz, 1H), 6.50 (d, J=1 Hz, 1H), 6.43 (dd, J=4, 1 Hz, 1H), 2.78 (s, 3H), 2.35 (s, 3H); EIMS 270 m/z. Anal. (C$_{18}$H$_{26}$N$_2$ C$_4$H$_8$O$_8$ ¼H$_2$O) C, H, N.

EXAMPLE 5

(+)-3,3-Dimethylamino-17-methylmorphinan sesquitartrate

To a solution of 0.52 g (2 mmol free base) 5 in 10 mL acetonitrile, 2.4 mL 37% formaldehyde and 0.60 g (13 mmol) sodium cyanoborohydride were added at 0° C. The reaction mixture (pH 12) was stirred at 0° C. for 5 minutes and then allowed to warm to room temperature. After a reaction time of 30 minutes, 0.3 mL glacial acetic acid was added and the reaction mixture (pH 6) was stirred at room temperature for another 45 minutes. The volatiles were removed in vacuo and the residue was extracted with 1×20 mL 2N potassium hydroxide and 4×10 mL ether. The combined organic fraction was washed with 1×10 mL water, dried with sodium sulfate, and evaporated to pale yellow oil (0.53 g, 93%) which was nearly homogeneous by TLC. The crude free base was dissolved in hot 2-propanol and added to a solution of 0.57 g (4 mmol) D-(1)-tartaric acid in hot 2-propanol. The crystalline 7 (0.67 g, 65%) was carefully isolated under an atmosphere of argon (hygroscopic), mp 96°-99° C. $^1$H NMR (CDCl3) d 3.15 (s, 6H), EIMS 284 m/z. Anal. (C$_{19}$H$_{28}$N$_2$ C$_6$H$_9$O$_9$ ¼ H$_2$O) C, H, N.

EXAMPLE 6

(+)-3-Chloro-17-methylmorphinan fumarate

In an argon-purged round bottom flask, 16.0 mL acetonitrile, 0.8 mL t-butylnitrite (90%, 5.4 mmol) and 0.68 g (5.0 mmol) dried cuprous chloride were combined and warmed to 60° C. A solution of 1.0 g (4 mmol, free base) of 5 in 8.0 mL acetonitrile was added dropwise via addition funnel over 10 minutes and the reaction mixture was stirred at this temperature for 2 hours. The reaction mixture was cooled and poured into a separatory funnel into which 50 mL 10% sodium carbonate (w/v) were added. The aqueous layer was removed and the organic layer was saved. The aqueous layer was then washed with 3×30 mL ethyl acetate and the combined organic fraction was washed with 1×25 mL water, dried with sodium sulfate and evaporated to 0.98 g (89%) of crude 8 as a dark oil. Purification by gradient flash column chromatography (CHCl$_3$:CH$_3$OH:NH$_4$OH 95:5:1/90:10:1) yielded 0.59 g (55%) pure 8 as the free base. The free base (0.48 g, 1.7 mmol) was dissolved in a minimal volume of 2-propanol and added to a solution of 0.21 g fumaric acid (1.8 mmol) in 2-propanol. Addition of anhydrous ether resulted in crystalline 8. Recrystallization in 2-propanol gave 0.41 g (56%) pure 8, mp 136°-141° C. (If crystallization is difficult and the crude salt is dark, boiling in 2-propanol with charcoal followed by filtration over celite facilitates isolation of pure product. Ethyl acetate may also be used as a recrystallization solvent). IR (KBr, salt) 650 cm$^{-1}$ (C-Cl); $^1$H NMR (CDCl$_3$) d 7.25 (d, J=2 Hz, 1H), 7.14 (dd, J=6, 2 Hz, 1H), 7.08 (d, J=6 Hz, 1H), 2.62 (s, 3H); EIMS 275, 277 (M+2) m/z. Anal. (C$_{17}$H$_{22}$NCl C$_4$H$_4$O$_4$ 2 H$_2$O) C, H, N.

EXAMPLE 7

(+)-3-Isothiocyanato-17-methylmorphinan HCl

A solution of 0.26 g (1 mmol, free base) 5 in 24 mL pentene-stabilized chloroform was added to a solution of 0.32 g (2.8 mmol) sodium bicarbonate in 10 mL water at 0° C. The biphasic reaction mixture was stirred under an atmosphere of argon at 0° C. for 10 minutes. Freshly distilled thiophosgene (100 uL, 1.1 mmol) was added and the reaction mixture was stirred at 0° C. for 10 minutes and at room temperature for 30 minutes. The organic layer was removed and the aqueous layer was extracted with 2×10 mL chloroform. The combined organic fraction was washed with 1×10 mL water, dried on sodium sulfate and evaporated to 0.29 g (97%) orange foam. The crude free base was dissolved in a minimal volume of 2-propanol and acidified with a saturated solution of hydrochloric acid in 2-propanol (pH 4). Careful addition of anhydrous ether resulted in 0.15 g (45%) crystalline 9 mp d 260° C., IR (CHCl$_3$) 2160 (br); CIMS 299 m/z. Anal. (C$_{17}$H$_{22}$N$_2$S HCl 3/4 H$_2$O) C, H, N.

UTILITY

To be effective agents, anticonvulsant or neuroprotective agents must possess certain properties. The properties include: binding to a non-opiate receptor site in the brain, minimal toxicity to the recipient, absence of behavioral or performance detriments in the recipient, low dosimetry, ability to block the spread of seizures, and increase seizure threshold, blocking neurodegenerative mechanisms, improving cerebral blood flow, the agent should not be habit-forming, and the recipient should not become increasingly tolerant of the substance. Studies described in further detail below indicate that compounds of the present invention are useful and effective as anticonvulsant or neuroprotective agents based on evaluations of the factors cited herein. Studies confirming the biological activity and pharmacological utility of the compounds of this invention are described in the examples that follow.

The anticonvulsant activity of the present compounds was assessed by the method of inducing maximal electroshock seizures (MES) in rats using the standard testing protocol conditions hereinafter described:

Animals. Male Sprague-Dawley rats weighing 200-250 g obtained from Zivic Miller Laboratories, Alison Park, Pa., were used for all experiments. Upon delivery the animals were kept in individual pens housed in a temperature controlled laboratory. A standard 12-hour light-dark cycle was maintained. The animals were given food and water ad libitum.

Maximal electroshock seizure (MES) assay. Supramaximal (tonic hindlimb extension) seizures were induced in test rats by means of an electric shock apparatus. A current of 60 Hz and 50 mA was delivered transauricularly through miniature alligator clips attached to the pinna of each ear for 2.0 seconds. The shock parameters used in the studies have been shown to induce MES, and not threshold seizures. In general, MES causes a generalized convulsion characterized by an initial tonic forelimb extension (TFE) progressing immediately to tonic hindlimb extension (THE) followed by clonic jerking. The presence or absence of THE was recorded for each MES convulsion.

Experimental protocol. Two groups of animals with n=10 for each group were tested under the conditions described above. Compounds were administered to each test animal by a single subcutaneous injection. There were no signs of overt sedation, ataxia or motor impairment at any time during the MES assay after drug injection.

The anticonvulsant activity of compounds of the invention in comparison with dextromethorphan and dextrorphan as determined by the MES assay experimental protocol described above is summarized in Tables 2 and 3.

TABLE 2

| Compound | Anticonvulsant $ED_{50}$(mg/kg) |
|---|---|
| 1 | 38 |
| 2 | 5 |
| 5 | 25 |
| 7 | >25 |

Figure 2:
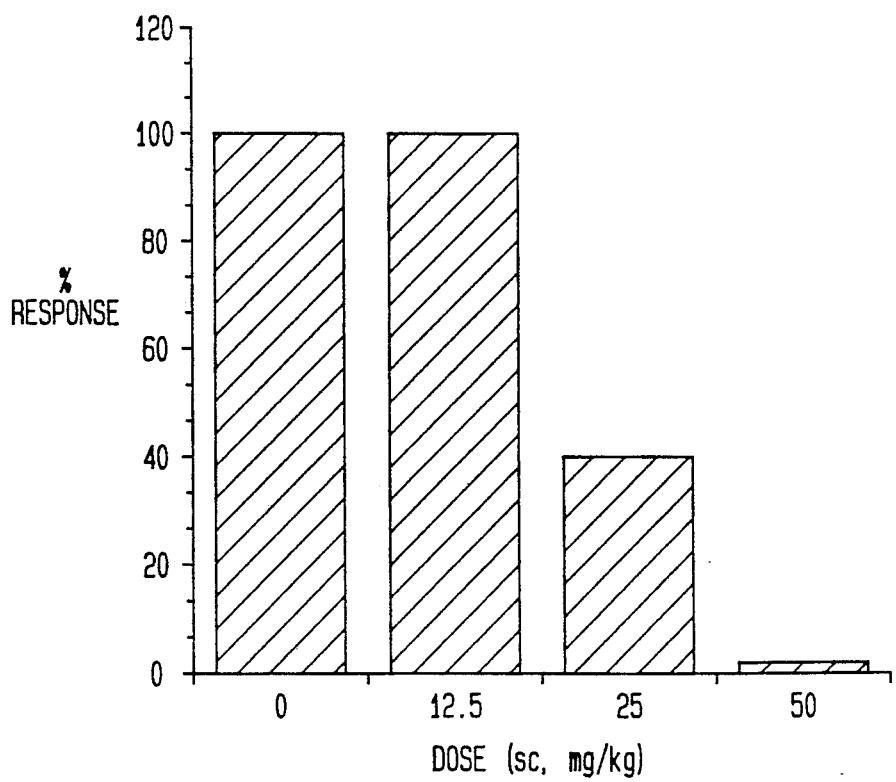
FIG. 2 is a bar diagram showing the presence of seizure activity as a function of the amount of Compound 5 of the invention administered.
Figure 3:
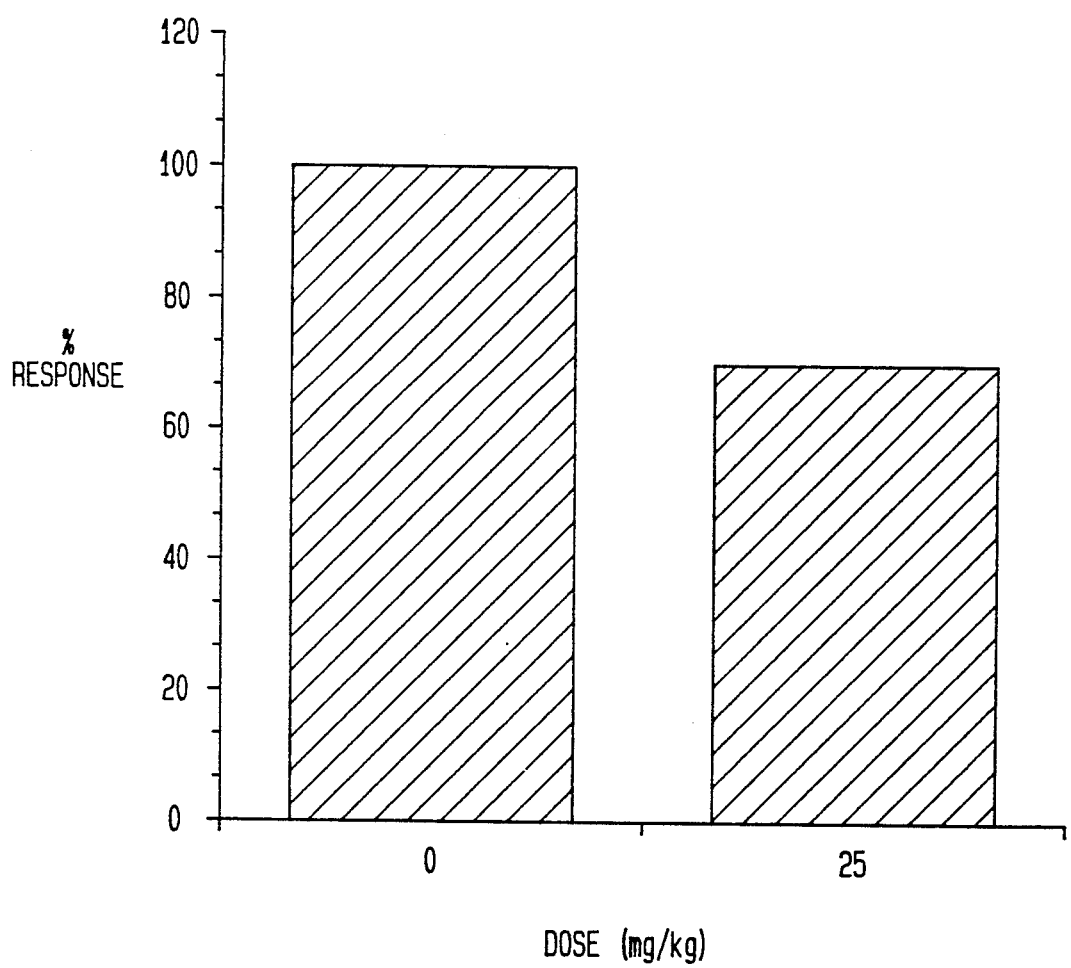
FIG. 3 is a bar diagram showing the presence of seizure activity as a function of the amount of Compound 7 of the invention administered.

In the following table, the results of the test protocol expressed in terms of seizure activity as a function of the amount of anticonvulsant agent administered, derived from FIGS. 1, 2 and 3, are set forth. It is to be emphasized here that at doses above about 60 mg/kg at which dextromethorphan inhibits seizures by about 70%, that dextromethorphan (compound 1) exhibits proconvulsant activity in mammals.

TABLE 3

Summary of effects of anticonvulsants on MES convulsions derived from FIGS. 1, 2 and 3.

| Compound | Dose, mg/kg | % Responding (THE) |
|---|---|---|
| 1 | 0 | 100 |
| 1 | 15 | 70 |
| 1 | 30 | 70 |
| 1 | 60 | 30 |
| 5 | 0 | 100 |
| 5 | 12.5 | 100 |
| 5 | 25 | 40 |
| 7 | 0 | 100 |
| 7 | 25 | 65 |

The invention has been described and illustrated with respect to certain specific embodiments. Those skilled in the art to which this invention pertains in its various aspects will appreciate that variations, modifications and substitutions can be made to specific aspects of the invention illustrated above without departing from the spirit of the invention. Such variations, modifications and substitutions are deemed to be within the scope of this invention, as limited only by the scope of the claims which follow.

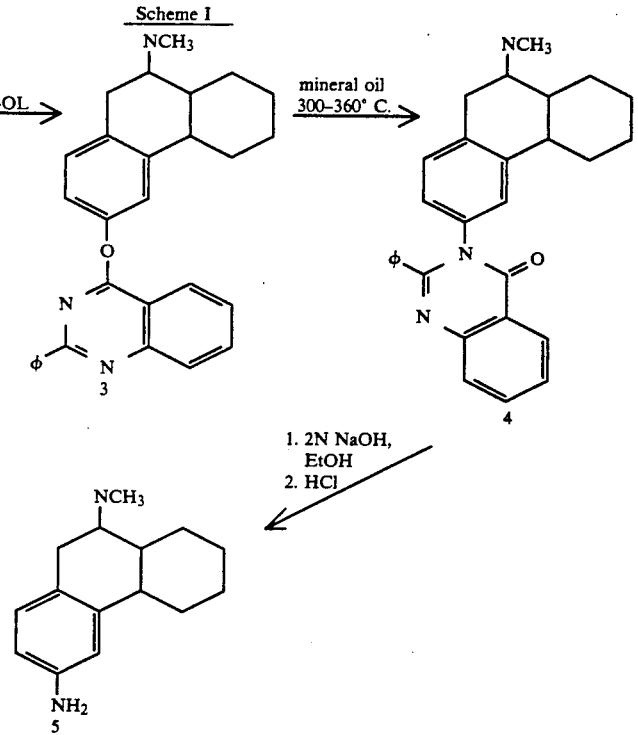

Scheme II -continued

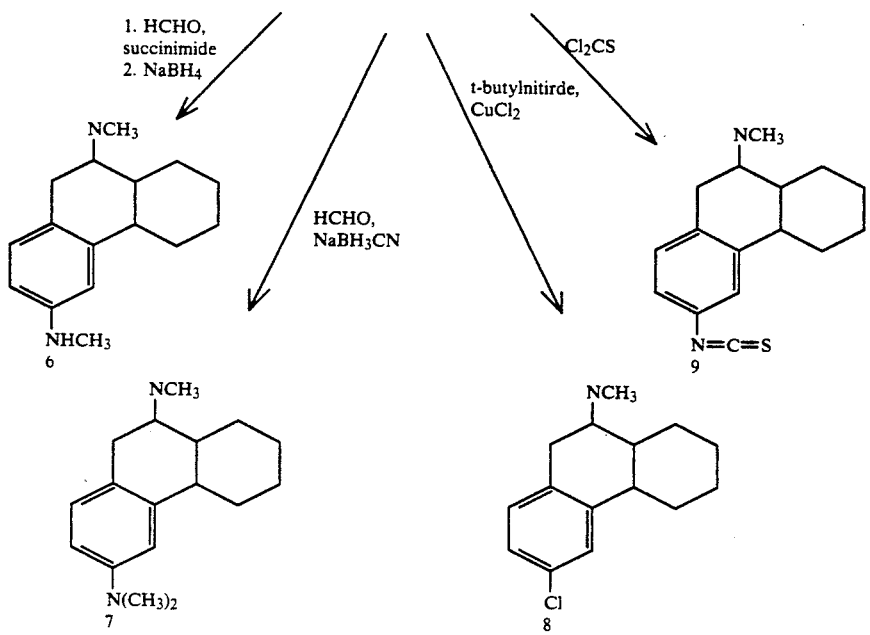

We claim:
1. A pure unnatural enantiomeric morphine compound having the formula:

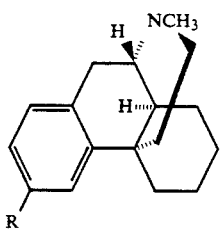

wherein the morphinan is (+)-3-dimethylamino-N-methylmorphinan in which R is dimethylamino, or a pharmaceutically acceptable acid addition salt thereof.

2. The compound of claim 1 contained in a liquid injectable dosage form.

3. The compound of claim 1 contained in a liquid oral dosage form.

4. The compound of claim 1 contained in a solid oral dosage form.

5. A method of treating a mammal for convulsions which comprises administering to said mammal an effective anticonvulsant or neuroprotective amount of a pure unnatural enantiomeric morphinan compound having the formula:

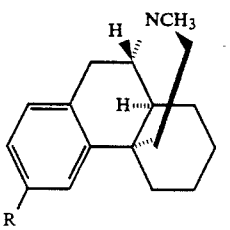

in which R is amino or dimethylamino, or a pharmaceutically acceptable acid addition salt thereof.

6. The method of claim 5 wherein the morphinan is (+)-3-amino-N-methyl morphinan.

7. The method of claim 5 wherein the morphinan is (+)-3-dimethylamino-N-methylmorphinan.

8. The method of claim 5 wherein the effective anticonvulsive or neuroprotective amount is dosage between 1 and 1000.0 mg of active ingredient.

9. A process for preparing (+)-3,3-dimethylamino-N-methylmorphinan comprising the steps of:
(a) dissolving dextrorphan in a polar solvent and reacting the solution with a halogen-substituted quinazoline compound and a salt under inert gas to produce a (+)-3-quinazolinyloxy-N-methylmorphinan compound;
(b) placing the product thus formed in a nonpolar solvent under inert gas and heating the solution to a temperature between 300°-370° C. to produce (+)-3-[4-oxo-2-phenyl-3(4H)-quinazolinyl]-N-methylmorphinan;
(c) reacting the product of step (b) with a strong base in a polar protic solvent under inert gas;
(d) cooling the reaction mixture, adjusting the pH to 1-3 and stirring the resulting mixture at reflux under inert gas, resulting in an aqueous reaction mixture;
(e) cooling the aqueous reaction mixture, then extracting the mixture with an organic solvent and washing the resulting organic phase in acid and neutralizing the combined reaction to alkaline pH with base;
(f) extracting the resulting aqueous mixture in chloroform/methanol solvents;
(g) removing the solvents in vacuo to produce a free base;
(h) reacting the free base product of step (g) with formaldehyde and sodium cyanoborohydride, stirring the mixture at a temperature below ambient temperature and allowing the mixture to come to ambient temperature;

(i) adjusting the pH of the reaction mixture to 4.5–6.5;

(j) removing volatile components in vacuo and extracting the residue with an aqueous base and an organic solvent;

(k) washing the extracted fraction with water, drying the fraction, and evaporating it to a crude free base in an oil form;

(l) dissolving the free base in acidified polar solvent to form a crystalline product.

10. The process of claim 9 wherein the nonpolar solvent of step (b) is mineral oil.

* * * * *